United States Patent [19]

Connor et al.

[11] Patent Number: 5,215,986

[45] Date of Patent: Jun. 1, 1993

[54] 5-HYDROXY-2-PYRIMIDINYLMETHYLENE OXAZA HETEROCYCLES

[75] Inventors: David T. Connor, Ann Arbor; Catherine R. Kostlan, Saline, both of Mich.; Gary P. Shrum, Fairfield, Ohio; Paul C. Unangst, Ann Arbor, Mich.

[73] Assignee: Warner-Lambert Company, Morris Plains, N.J.

[21] Appl. No.: 891,611

[22] Filed: Jun. 1, 1992

[51] Int. Cl.$^5$ ............... A61K 31/535; A61K 31/55; A61K 31/505; C07D 265/00; C07D 239/02

[52] U.S. Cl. .................... 514/228.8; 514/211; 514/269; 540/544; 544/63; 544/298

[58] Field of Search ............. 544/298, 63; 540/544; 514/211, 228.8, 269

[56] References Cited

U.S. PATENT DOCUMENTS 4,892,870 1/1990 Lee .......................... 514/211

Primary Examiner—Cecilia Tsang
Attorney, Agent, or Firm—Ronald A. Daignault

[57] ABSTRACT

Novel 5, 6, or 7 membered oxaza heterocycles substituted at the 4-carbon by a 5-hydroxypyrimidinylmethylene group inhibitors of 5-lipoxygenase and/or cyclooxygenase and are thus useful in treating inflammatory diseases are described as well as pharmaceutical compositions, methods of manufacture of the compounds, and compositions and methods of treating the noted diseases.

6 Claims, No Drawings

5-HYDROXY-2-PYRIMIDINYLMETHYLENE OXAZA HETEROCYCLES

BACKGROUND OF THE INVENTION

The present invention concerns novel compounds which are 5-hydroxy-2-pyrimidinylmethylene oxaza heterocycles, which are five, six, and seven membered rings belonging to the 3-isoxazolidinone, 2H-1,2-oxazin 3(4H) one and 3-isoxazepinone class, and pharmaceutically acceptable acid addition or base salts thereof, pharmaceutical compositions and methods of use therefor. The compounds of the present invention have activity as inhibitors of 5-lipoxygenase and/or cyclooxygenase providing treatment of conditions advantageously affected by such inhibition including inflammation, arthritis, pain, fever, and particularly rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is in treating inflammatory conditions. Thus, the present invention is also a pharmaceutical composition or method of manufacturing a pharmaceutical composition for the use of treating the noted conditions.

3,5-Di-tertiarybutyl-4-hydroxyphenyl substituted oxaza heterocycles are known to provide in vivo antiinflammatory activity as described in U.S. Pat. No. 4,892,870.

Various 5-hydroxypyrimidines are described in copending U.S. application Ser. Nos. Numbers 648,114, and 648,115 of Jan. 31, 1991, No. 756,400 of Sep. 9, 1991, No. 840,360 of Feb. 24, 1992, and No. 847,511 of Mar. 6, 1992. These compounds are also active as inhibitors of 5-lipoxygenase and/or cyclooxygenase. Such disclosed pyrimidines may also be substituted at the 4- and/or 6- positions with various alkyl groups. Yet none show the present 2-substituted oxaza heterocycles interrupted by vinyl.

SUMMARY OF THE INVENTION

Accordingly, the present invention are compounds of the formula

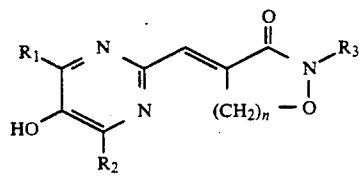

wherein n is an integer of 1-3;

$R_1$ and $R_2$ are each independently hydrogen or lower alkyl;

$R_3$ is hydrogen, lower alkyl, lower alkenyl or cycloalkyl of 3-6 carbon atoms, and pharmaceutically acceptable acid addition and base salts.

The present invention is also a pharmaceutical composition for the treatment of conditions advantageously affected by the inhibition of 5-lipoxygenase and/or cyclooxygenase which comprises an amount effective for the treatment of the condition of a compound of the formula I and the pharmaceutically acceptable acid addition or base salt thereof together with a pharmaceutically acceptable carrier. The condition is meant to include, for example, arthritis or other inflammatory diseases, allergic diseases, pain, fever, and psoriasis, but preferably inflammatory diseases.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of medical therapeutic agent.

Pharmaceutical composition or use of the compound or salt of formula I is meant to include treatment understood to be prophylactic pertinent to the foregoing named condition.

Compounds of the formula I in this invention are inhibitors of the synthesis of the products of the enzymes 5-lipoxygenase and/or cyclooxygenase, and will be useful for the treatment of rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia induced cell damage particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is in treating inflammatory conditions.

DETAILED DESCRIPTION

The compounds of formula I, may in certain cases be isolated in two geometric, isomeric forms identified hereinafter as Isomer-E and Isomer Z. These isomers correspond to known isomeric forms but their precise structures are new and as such they are considered to be novel compounds falling within the scope of this invention. The preferred geometric form is the E form.

The term "lower alkyl" refers to a straight or branched chain alkyl of from about 1-7 carbon atoms. Typical of the alkyl radicals intended are, for example, methyl, ethyl, tertiary butyl, n-pentyl, isopentyl, hexyl, isohexyl, heptyl, and the like.

Typical of the "lower alkenyl" radicals intended are those of from about 2-5 carbon atoms such as vinyl, allyl, isoprenyl, 2-butenyl, 3-methyl 2-butenyl, and 3-pentenyl or the like.

"Cycloalkyl of 3-6 carbon atoms" includes cyclopropyl, cyclobutyl, cyclopentyl, and cyclohexyl.

Appropriate compounds of formula (I) are also useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfamate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as argininine and lysine; guanidine; choline; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

Preferred embodiments of the present invention are compounds of the formula I wherein n is an integer of 1-3, $R_1$ and $R_2$ are each lower alkyl, and $R_3$ is hydrogen or lower alkyl.

More preferred are compounds of formula I wherein n is an integer of 1-3, $R_1$ and $R_2$ are each tertiary-butyl, and $R_3$ is hydrogen or lower alkyl.

Most preferred is (E)-4[[4,6-bis(1,1-dimethylethyl)-5-hydroxy-2-pyrimidinyl]methylene]tetrahydro-2-methyl-2H-1,2-oxazin-3-one.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffering from, or likely to suffer from any condition as described hereinbefore is 0.1 µg 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng-100 µg of the compound per kilogram, typically about 0.1 µg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in a aqueous liquid or nonaqueous liquid; or in the form of an oil-in water emulsion or a water-in-oil emulsion. The active ingredient may also be in the form of a bolus, electuary, or paste.

The usefulness of the compounds of the present invention as inhibitors of the 5-lipoxygenase or cyclooxygenase enzymes, or in treating related diseases or conditions, may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL 1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air 5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2\times10^6$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at $-20°$. Aliquots (100 μl) are analyzed for $LTB_4$ and $PGF_{2\alpha}$ using radioimmunoassay kits as provided by the supplier.

Biochemical data obtained from this whole cell assay may be shown as $IC_{50}$s which are calculated as the amount of test compound causing 50% inhibition of $LTB_4$ or $PGF_{2\alpha}$ formation.

Thus, for example, a representative compound of the present invention, (E)-4[[4,6-bis(1,1-dimethylethyl)-5-hydroxy-2-pyrimidinyl]methylene]tetrahydro-2-methyl-2H 1,2-oxazin-3-one, when tested as above described, showed 84% inhibition at 10 μm concentration for ARBL and 88% inhibition at 10 μm for ARBC.

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free $-CH(CH_3)COOH$ or $-CH_2CH_2COOH$ group (which optionally can be in the form of a pharmaceutically acceptable salt group, e.g., $-CH(CH_3)COO^-NA^+$ or $CH_2CH_2COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free $-CH_2COOH$ group (which optionally can be in the form of a pharmaceutically acceptable salt group, e.g. $-CH_2COO^-Na^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

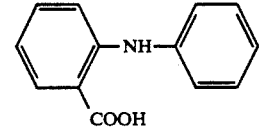

which can bear a variety of substituents and in which the free $-COOH$ group can be in the form of a pharmaceutically acceptable salt group, e.g., $-COO^-Na^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

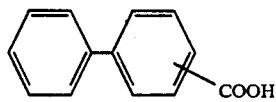

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

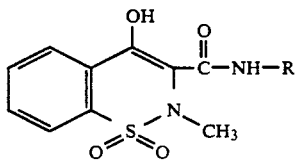

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H$_1$ or H$_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a K$^+$/H$^+$ ATPase inhibitor such as omeprazole, disclosed in U.S. Pat. No. 4,255,431, and the like. Each of the references referred to in this paragraph is hereby incorporated herein by reference.

The compounds of the present invention may be prepared by condensing a 5-hydroxy pyrimidine 2-aldehyde with a heterocyclic α-halo carbonyl compound in the presence of zinc according to the Reformatsky reaction, followed by dehydration of the hydroxymethylene intermediate as shown by the following reaction sequence.

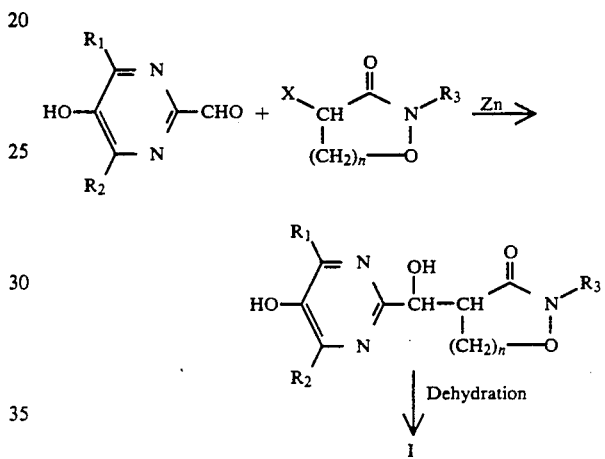

"X" in the above scheme is halo such as fluoro, chloro, bromo, or iodo, preferably bromo, and R$_1$, R$_2$, R$_3$, and n are as defined above. The condensation step can be enhanced by conducting the reaction at the boiling point of a suitable inert solvent such as toluene.

Dehydration is carried out by refluxing the hydroxymethylene intermediate under acidic conditions to facilitate removal of water. A suitable acidic reagent, for example, is p toluenesulfonic acid monohydrate. The reaction again can be run in a suitable inert solvent. Toluene is preferred since water can be removed by azeotropic distillation during the reaction.

The halocarbonyl starting materials are prepared by treating a hydroxylamine with a di haloalkanoyl halide as follows:

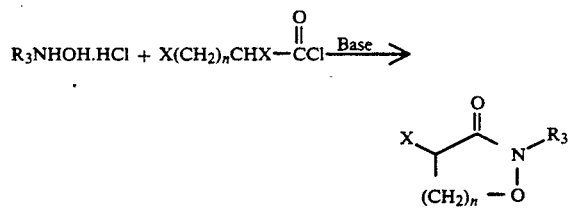

wherein X is halo, preferably bromo, and R$_3$ and n are as defined above. Suitable bases are alkali metal hydroxides or carbonates, e.g. sodium hydroxide or potassium carbonate and an inert solvent is also employed such as, for example, methylene chloride.

The 5-hydroxy pyrimidine starting materials used to prepare the compounds of formula I may be prepared as follows: where $R^1$ or $R^2$ are H or lower alkyl other than tertiarybutyl as shown in Scheme I from pyrimidines 9 which may be prepared as described by Hurst (*Heterocycles* 22(1), (1984)) for $R^1=R^2=$methyl.

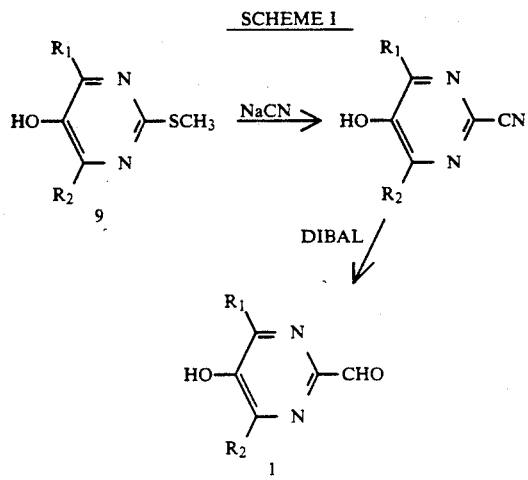

Starting pyrimidines where $R^1$ and $R^2$ are tertiarybutyl may be prepared as shown in Scheme II.

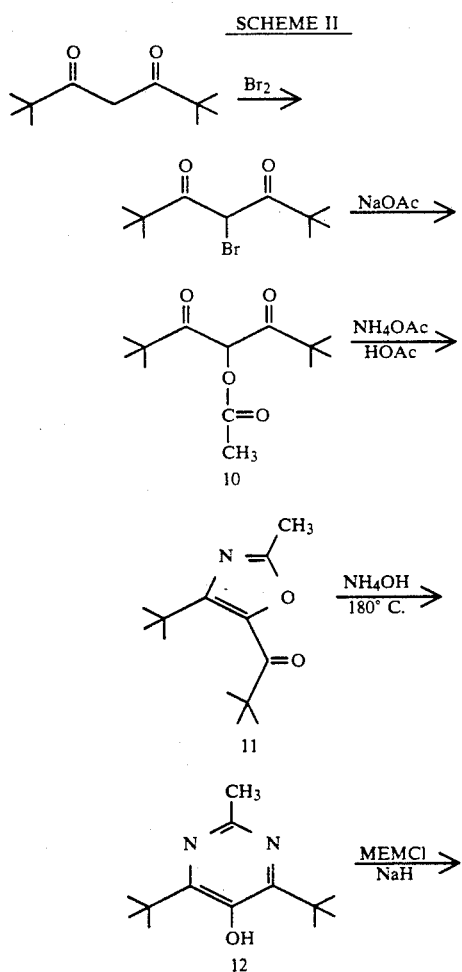

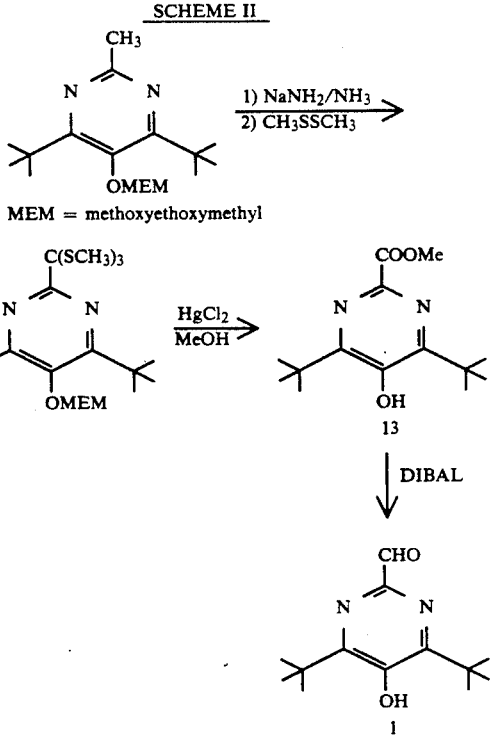

MEM = methoxyethoxymethyl

Compounds of the formula 10 in Scheme II is prepared from the known haloketone (C. W. Shoppee and D. Stevenson, *J. Chem. Soc. Perkin I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 10 is converted to oxazole 11 by treatment with an ammonium salt such as ammonium chloride or preferably ammonium acetate in a solvent such as acetic acid at reflux for 1 to 16 hours or in a solvent such as formamide at 100° to 200° C. for 1 to 6 hours. The oxazole 11 is converted to pyrimidine 12 by treatment with ammonia or an ammonium salt at elevated temperature. Preferably 11 is reacted with concentrated ammonium hydroxide at 150° to 190° C. in a pressure reaction vessel for 6 to 72 hours.

Pyrimidine 12 is then converted to the 2-carboxymethyl ester of the desired pyrimidine 13 in three steps which requires protection of the 5-hydroxy group, converting the 2-methyl group first to the methyl thioortho ester and hydrolysis with mercuric chloride in methanol to provide the desired ester. The ester 13 may be directly converted to the desired aldehyde starting material 1 of Scheme I by reducing the carboxymethyl group with diisobutylaluminum hydride, DIBAL.

The invention is further illustrated by the following representative examples.

EXAMPLE 1

4-Bromotetrahydro-2-methyl-2H-1,2-oxazin-3-one

A mixture of 65 mL of dichloromethane and 2.6 g (33 mmol) of 50% aqueous sodium hydroxide in 8 mL of water was treated with 2.5 g (30 mmol) of N-methylhydroxylamine hydrochloride. After cooling to 5° C., 8.5 g (32 mmol) of 2,4-dibromobutyryl chloride* was added dropwise, with the temperature maintained at 5° to 8°

C. An additional 2.6 g of 50% aqueous sodium hydroxide was added, and the mixture was stirred for 2 hours at 5° C. A final 2.6 g of 50% aqueous sodium hydroxide was added, and the mixture was stirred at room temperature for 18 hours. The organic layer was separated, and the aqueous layer was extracted with dichloromethane. The combined organic layers were dried (anhydrous magnesium sulfate) and evaporated.

* H. Ikuta, H. Shirota, S. Kobayashi, Y. Yamagishi, K. Yamada, I. Yamatsu, and K. Katayama. J. Med. Chem., 30, 1995 (1987).

The residue was purified by flash chromatography (silica gel, 15% ethyl acetate in hexane elution) to yield 1.5 g (24%) of the title compound as an oil; $^1$H NMR (deuteriochloroform) δ 2.20 2.80 (m, 2H), 3.18 (s, 3H), 4.13 (m, 2H), 4.52 (m, 1H); MS m/e 194 (M+).

EXAMPLE 2

4,6-Bis(1,1-dimethylethyl)-5-[(2-methoxyethoxy)methoxy]-2 pyrimidine carboxylic acid thiomethyl orthoester To a solution of sodium amide (602 mmol) in liquid ammonia is added 4,6-bis (1,1 dimethylethyl)-5-[(2-methoxyethoxy)-methoxy] -2-methylpyrimidine (53.4 g, 172.0 mmol) dissolved in 50 mL of THF.

The reaction mixture is stirred for one half hour and then cooled to −78° C. Dimethyldisulfide (50.2 g, 533.2 mmol) is added to the reaction mixture over 20 minutes. When addition is complete, the reaction mixture is warmed to reflux for 1 hour.

The reaction is quenched by the slow addition of 27 g of solid NH$_4$Cl and the NH$_3$ is evaporated through a trap containing 500 mL of 10% (W/V) aqueous NaOH. The reaction mixture is partitioned between 200 mL of Et$_2$O and 200 mL of 1.0N NaOH. The aqueous layer is extracted with Et$_2$O (3×200 mL). The combined organic extracts are washed with 1.0N NaOH (2×100 mL) and 100 mL of brine. Drying over MgSO$_4$ and evaporation of the solvent gives 80.5 g (100%) of the desired orthoester as an oil.

EXAMPLE 3

4,6-Bis-(1,1-dimethylethyl)-5-hydroxy-2-pyrimidine carboxylic acid methyl ester

HgCl$_2$ (73.05 g, 269.1 mmol) is added slowly to a solution of 4,6-bis-(1,1-dimethylethyl)-5-[(2-methoxyethoxy)methoxy]-2-pyrimidine carboxylic acid thiomethyl orthoester (80.5 g, 179.4 mmol) in 400 mL of MeOH at room temperature and the reaction mixture is stirred for 1 additional hour.

The reaction mixture is diluted with 400 mL of CH$_2$Cl$_2$ and stirred for 10 minutes. The precipitate is removed b filtration through celite and the filtrate is concentrated on the rotovap. The residue is taken up in 300 mL of CH$_2$Cl$_2$ and washed with saturated NH$_4$Cl (3×100 mL). Drying over MgSO$_4$ and evaporation of the solvent gives a brown solid. Recrystallization from 200 mL of hexane gives 30.0 g (63%) of the desired ester; mp 131°–133° C.

EXAMPLE 4

4,6-Bis-(1,1-dimethylethyl)-5-[(2-methoxyethoxy)methoxy]-2-pyrimidine carboxylic acid methyl ester 4,6-Bis-(1,1-dimethylethyl)-5-[(2-methoxyethoxy)methoxy]-2-pyrimidine carboxylic acid thiomethyl orthoester (41.8 g, 93.1 mmol) is dissolved in 400 mL of 5% H$_2$O/MeOH, and cooled in a dry ice/acetone bath to 40° C. H$_2$O (32.3 g, 149.0 mmol) and HgCl$_2$ (101.2 g, 372.6 mmol) are added to the reaction mixture, and the dry ice/acetone bath is removed. The solution is allowed to warm to room temperature for 1 hour. The reaction mixture is diluted with 500 mL of CH$_2$Cl$_2$ and stirred for 5 minutes. The solid is removed by filtration, and the filtrate is concentrated on the rotovap. The residue is taken up in 500 mL of CH$_2$Cl$_2$ and washed with saturated NH$_4$Cl (2×200 mL) followed by 100 mL of brine. Drying over MgSO$_4$ and evaporation of solvent gives a yellow oil. Flash chromatography in Et$_2$O gives 23.9 g (79%) of the desired methyl ester.

EXAMPLE 5

4,6-Bis-(1,1-dimethylethyl)-5-[(2-methoxyethoxy)methoxy]-2-pyrimidine carboxaldehyde A solution of di-isobutylaluminum hydride (22.6 mL, 1.5M in toluene) is added slowly (over a period of 30 minutes) to a solution of 4,6-bis-(1,1-dimethylethyl)-5-[(2-methoxyethoxy)methoxy]-2-pyrimidine carboxylic acid methyl ester (10.0 g, 28.2 mmol) in 100 mL of toluene at 78° C. under an argon atmosphere.

After 3 hours, additional di isobutylaluminum hydride (6.2 mL, 1.5M, in toluene) is added to this reaction mixture at −78° C., and the mixture is stirred at −78° C. for an additional 2 hours. The reaction is quenched with 100 mL of 10% HOAc/H$_2$O, and the mixture is warmed to room temperature. The organics are extracted into Et$_2$O (3×100 mL). The combined organic layers are washed with 100 mL of 10% HOAc/H$_2$O followed by 100 mL of brine. Drying over MgSO$_4$ followed by evaporation of solvent gives 8.9 g (97%) of the desired aldehyde as an oil.

EXAMPLE 6

4,6-Bis(1,1-dimethylethyl)-5-hydroxy-2-pyrimidine carboxaldehyde

Trifluoroacetic acid (1.05 g, 9.2 mmol) is added to a solution of 4,6-bis(1,1-dimethylethyl)-5-[(2-methoxyethoxy)methoxy]-2-pyrimidine carboxaldehyde (1.0 g, 3.1 mmol) in methylene chloride and the reaction mixture is stirred at room temperature for 5 hours. The reaction mixture is neutralized by the addition of saturated aqueous NaHCO$_3$ and the layers separated. The organic layer is washed with brine (50 mL), dried over MgSO$_4$, and evaporated. Recrystallization of the residue from hexane gives pure 4,6-bis(1,1-dimethylethyl)-5-hydroxy-2-pyrimidine carboxaldehyde (0.24 g, 33%); mp 187°–189° C.

EXAMPLE 7

4-[[4,6-Bis(1,1-dimethylethyl)-5-hydroxy-2-pyrimidinyl]hydroxymethyl]tetrahydro-2-methyl-2H-1,2-oxazin-3-one A mixture of 1.1 g (5.7 mmol) of 4-bromo tetrahydro-2-methyl 2H 1,2-oxazin-3-one, Example 1, 1.2 g (5.1 mmol) of 4,6-bis(1,1-dimethylethyl)-5-hydroxy-2-pyrimidinecarboxaldehyde, Example 6, and 0.75 g (11 mmol) of zinc dust in 30 mL of toluene was stirred at reflux for 18 hours. The cooled reaction mixture was diluted with dichloromethane and vigorously stirred. The zinc was filtered and washed with dichloromethane. The combined filtrates were evaporated to a foam. The residue was purified by flash chromatography (silica gel, 15% ethyl acetate in hexane elution) to give 0.70 g (39%) of the title compound as an oil mixture of diastereomers; MS m/e 352 (M+1).

EXAMPLE 8

(E)-4-[[4,6-Bis(1,1-dimethylethyl)-5-hydroxy-2-pyrimidinyl]methylene]tetrahydro-2-methyl-2H-1,2-oxazin-3-one A mixture of 0.70 g (2.0 mmol) of 4-[[4,6-bis(1,1-dimethylethyl)-5-hydroxy-2-pyrimidinyl]hydroxymethyl]-tetrahydro-2-methyl-2H-1,2-oxazin-3-one, Example 7, and 0.040 g (0.20 mmol) of p-toluenesulfonic acid monohydrate in 15 mL of toluene was stirred at reflux for 18 hours. The cooled reaction mixture was evaporated, and the residue was purified by flash chromatography (silica gel, 15% ethyl acetate in hexane elution) to yield 0.20 g (31%) of the title compound, mp 180°–181° C.; $^1$H NMR (deuteriochloroform) δ 1.46 (s, 18H), 3.36 (s, 3H), 3.46 (m, 2H), 4.21 (m, 2H), 5.25 (s, 1), 7.73 (s, 1H); MS m/e 334 (M$^+$ +1).

Anal. Calc. for ($C_{18}H_{27}N_3O_3$):

C, 64.84; H, 8.16; N, 12.6;

Found: C, 64.80; H, 8.08; N, 12.36.

What is claimed is:

1. A compound of the formula

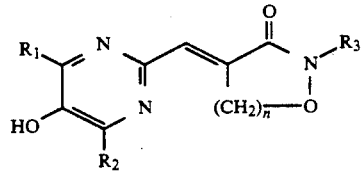

wherein n is an integer of 1–3;

$R_1$ and $R_2$ are each independently hydrogen or lower alkyl;

$R_3$ is hydrogen, lower alkyl, lower alkenyl or cycloalkyl of 3–6 carbon atoms, or a pharmaceutically acceptable acid addition or base salt thereof.

2. A compound of claim 1 wherein $R_1$ and $R_2$ are each lower alkyl and $R_3$ is hydrogen or lower alkyl.

3. A compound of claim 2 wherein $R_1$ and $R_2$ are each tertiary-butyl and $R_3$ is hydrogen or lower alkyl.

4. A compound of claim 3 and being (E)-4[[4,6-bis(1,1-dimethylethyl)-5-hydroxy-2-pyrimidinyl]methylene]tetrahydro-2-methyl-2H-1,2-oxazin-3-one.

5. A pharmaceutical composition for the treatment of a condition advantageously affected by the inhibition of 5-lipoxygenase, cyclooxygenase or both 5-lipoxygenase and cyclooxygenase which comprises an amount effective for the treatment of the condition of the compound of claim 1 and a pharmaceutically acceptable carrier.

6. A method of treating inflammation in a human in need of such treatment which comprises administering a compound of claim 1 in unit dosage form.

* * * * *